US006914168B2

(12) United States Patent  (10) Patent No.: US 6,914,168 B2
Pilling et al.  (45) Date of Patent: Jul. 5, 2005

(54) ARTICLES FOR THERAPEUTIC PARAFFIN TREATMENT AND METHODS OF USE

(75) Inventors: Melanie Pilling, Green Bay, WI (US); David W. Albers, Green Bay, WI (US); Jean Claus, Green Bay, WI (US)

(73) Assignee: Little Rapids Corporation, Green Bay, WI (US)

( * ) Notice: Subject to any disclaimer, the term of this patent is extended or adjusted under 35 U.S.C. 154(b) by 144 days.

(21) Appl. No.: 10/402,102

(22) Filed: Mar. 28, 2003

(65) Prior Publication Data

US 2005/0049659 A1 Mar. 3, 2005

(51) Int. Cl.[7] .............................. A61F 7/00; A61F 13/00
(52) U.S. Cl. ............................. 602/51; 602/48; 607/96; 607/108; 607/112
(58) Field of Search .......................... 607/96, 108–112; 126/400; 602/41, 48, 51; 426/486; 428/486

(56) References Cited

U.S. PATENT DOCUMENTS

| 1,264,781 | A |   | 4/1918  | Ehrhardt        |        |
|-----------|---|---|---------|-----------------|--------|
| 1,620,539 | A |   | 3/1927  | Gernsback       |        |
| 2,226,842 | A |   | 12/1940 | Brandt          |        |
| 2,377,774 | A |   | 6/1945  | Gotham          |        |
| 2,425,696 | A |   | 8/1947  | Herrmann et al. |        |
| 2,572,641 | A | * | 10/1951 | Manley          | 602/51 |
| 2,954,324 | A |   | 9/1960  | Brummer         |        |
| 3,298,368 | A |   | 1/1967  | Charos          |        |
| 3,470,877 | A |   | 10/1969 | Morgan          |        |
| 4,149,536 | A |   | 4/1979  | Villard         |        |
| 4,253,983 | A | * | 3/1981  | Blanie          | 252/70 |
| 4,282,877 | A |   | 8/1981  | Mathews         |        |
| 5,847,363 | A | * | 12/1998 | Debourg et al.  | 219/424 |
| 5,891,116 | A |   | 4/1999  | Mast            |        |
| 6,027,513 | A |   | 2/2000  | Massana Florensa |       |
| 6,053,649 | A |   | 4/2000  | Ronai           |        |

OTHER PUBLICATIONS

Annette Stucky, How to Make a Home Paraffin Bath, Date Unknown, physical therapy .about.com, U.S.

* cited by examiner

Primary Examiner—Roy D. Gibson
(74) Attorney, Agent, or Firm—Nicholas A. Kees; Godfrey & Kahn, S.C.

(57) ABSTRACT

A method for providing a paraffin treatment to a patient, including the steps of: (a) melting a paraffin composition to a melted, flowable state; (b) immersing at least a portion of an absorptive strip into the melted paraffin composition so that the strip absorbs some of the melted paraffin composition; (c) applying the strip containing the melted paraffin composition to a portion of skin on the patient; (d) allowing the strip containing the melted paraffin composition to remain in contact with the portion of skin whereby the melted paraffin transfers heat to the patient's skin; and (e) removing the strip from the portion of the patient's skin wherein the paraffin composition is contained by the strip making removal of strip and paraffin composition substantially simultaneous. The present invention is also directed to a therapeutic strip, containing melted paraffin, to be applied to a portion of a patient's skin to provide a therapeutic treatment of heat to the patient.

14 Claims, 2 Drawing Sheets

ARTICLES FOR THERAPEUTIC PARAFFIN TREATMENT AND METHODS OF USE

FIELD OF THE INVENTION

This invention relates generally to therapeutic treatments. In particular, the invention is directed to articles and methods for providing hot paraffin treatments.

BACKGROUND OF THE INVENTION

It is well known that hot paraffin or, alternatively, wax has many therapeutic properties and provides many benefits when applied to the human body. One such benefit is moisturizing the skin. Further, removing solidified paraffin has an exfoliating effect. Consequently, skin treated with hot paraffin is said to have a silk like feel. As a result, paraffin treatments are commonplace in spas and other homeopathic treatment facilities.

Another therapeutic benefit of hot paraffin treatment is obtained by heating a patient's body parts, particularly joints and muscles. The penetrating heat from hot paraffin helps relieves pain and stiffness in afflicted joints, relaxes muscles, reduces muscle spasms, and stimulates blood circulation to the affected area. Paraffin treatments are therefore useful before or after exercise, massage or other physical therapy. In addition, paraffin treatments are used in the symptomatic relief of pain due to arthritis, bursitis, fibrositis, tendonitis, chronic joint inflammation, muscle strains, sprains, or spasms, and additional athletic conditions in which heat therapy is recommended and beneficial. Paraffin treatment is frequently prescribed for post-fracture and post dislocation treatment.

Traditionally, paraffin for therapeutic purposes has been applied to the human body by dipping body parts into paraffin warmed to a flowable state. The body part is subsequently withdrawn and the paraffin allowed to at least partially solidify. Further benefit may be had by repeatedly dipping and cooling additional layers of paraffin onto the body part to increase the heat content conveyed to the patient. However, the traditional approach leaves much to be desired.

First, due to the need to physically dip the body portion in flowable paraffin, applying paraffin to many body parts, such as the knee or shoulder joint, is difficult. Although hot paraffin may be blotted or painted onto a body part, such an approach does not promote uniform coverage and, thusly, uneven transfer of heat to underlying joints and tissues results. Also, heat is lost during the blotting or painting which reduces the beneficial effects of the hot paraffin treatment. Painting and blotting further causes unwanted waste of the paraffin due to handling by blotter or brush and spattering of hot paraffin in unintended directions.

Second, regardless of the application method, hot paraffin comes into direct contact with the human body in the traditional process. Of course, once the paraffin dries and the treatment is deemed completed, the paraffin must be removed from the body. In the past, removal has been by way of simply peeling solidified paraffin from the body part. Unfortunately, traditional paraffin treatments require time-consuming clean-up of both patient and workplace because removal of solidified paraffin by peeling often creates small fragments of paraffin that attach to the patient's skin or fall away into the workplace.

Accordingly, a need exists for a method for hot paraffin treatment that does not entail dipping a body portion into hot paraffin. It would be desirable to have a process where hot paraffin could be applied to a selected body part in an even and controlled manner. A process that maximizes the heat delivered to the body part would be especially advantageous. In addition, a method providing improved paraffin removal from the body part would be further desirable. Finally, a method providing reduced or minimal clean-up of paraffin following the treatment is needed.

SUMMARY OF THE INVENTION

In general, the present invention encompasses methods and articles for providing therapeutic paraffin treatments to patients. In one embodiment, a method for providing a paraffin treatment to a patient includes melting a paraffin composition to a flowable state. Then, at least a portion of an absorptive strip is immersed into the melted paraffin composition so that it absorbs some of the paraffin. The strip containing the melted paraffin composition is then applied to a portion of skin on the patient. After the strip containing the melted paraffin composition remains in contact with the portion of skin for a time sufficient for the melted paraffin to transfer heat to the patient's skin, the strip may be removed from the portion of the patient's skin wherein the paraffin composition is contained by the strip making removal of strip and paraffin composition simultaneous.

In one embodiment of the invention, the strip containing the melted paraffin composition remains in contact with said portion of skin for a sufficient amount of time for said paraffin composition to solidify before removal. In a preferred embodiment, the strip containing the melted paraffin composition remains in contact with said portion of skin for at least five (5) minutes.

In another embodiment, the portion of skin on which said strip containing the melted paraffin composition is applied overlies a body part including at least a finger joint, a wrist, an elbow, a shoulder, a neck, a backbone, a hip, a knee, an ankle, or a toe joint. In yet another embodiment, the portion of patient's skin continuously extends around a body part and the application of said strip containing the melted paraffin composition includes wrapping the strip around said body part to form said strip containing the melted paraffin composition into a wrap surrounding said body part.

According to the present invention, a single strip may be applied to the patient's skin to effectuate treatment or, in another embodiment, a plurality of strips may be applied to the skin of the patient.

In a preferred method, the absorptive strip is comprised by paper. In a more preferred embodiment, the paper has a paraffin absorptive capacity in the range of about six (6) to ten (10) grams paraffin per gram material of paper. The strips may be supplied for application individually or, alternatively, by a clip or roll comprising a continuous sheet of absorptive strips wherein the strips may be optionally separable by perforations.

The present invention is also directed to a therapeutic paraffin strip to be applied to a portion of a patient's skin to provide a therapeutic paraffin treatment to the patient as described and claimed herein. A therapeutic paraffin strip according to the present invention includes: (a) an absorptive strip; and (b) a melted paraffin composition contained within at least a portion of the strip. The therapeutic paraffin strip is applied to the portion of the patient's skin such that the heat of the melted paraffin composition is transferred to the portion of the patient's skin to provide a therapeutic treatment according to the invention. The paraffin strip may take the form of a wrap applied around a patient's body part.

In another embodiment of the present invention, a method for providing therapeutic paraffin treatment includes the melting of a paraffin composition to a melted, flowable state. At least a portion of a stretchable, absorptive strip is immersed into the melted paraffin composition, so that some of the paraffin composition is absorbed into the strip. The strip containing the melted paraffin composition is then applied to a portion of skin on the patient wherein the portion of skin overlies a body part including at least a finger joint, a wrist, an elbow, a shoulder, a neck, a backbone, a hip, a knee, an ankle, or a toe joint. After allowing the strip containing the melted paraffin composition to remain in contact with the portion of skin for a sufficient amount of time for the paraffin composition to solidify, so that the melted paraffin transfers heat to the patient's skin, the strip and paraffin composition are simultaneously removed from the portion of the patient's skin by simple removal of the strip itself.

Finally, the present invention encompasses a therapeutic regimen provided in a systematic manner to a patient that includes at least a therapeutic paraffin treatment as described and claimed herein.

Other objects, features and advantages of the present invention will become apparent after review of the specification, claims and drawings.

BRIEF DESCRIPTION OF THE DRAWINGS

It is understood that like reference characters refer to similar parts throughout the several figures.

DETAILED DESCRIPTION OF THE INVENTION

I. General

Before the present methods and materials are set forth, it is understood that this invention is not limited to the particular methodology or materials described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a strip" includes a plurality of such strips and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications and patents mentioned herein are incorporated herein by reference for the purpose of describing and disclosing methods and materials that are reported in the publications and patents which might be used in connection with the invention. Nothing herein is to be construed as an admission that the invention is not entitled to antedate such disclosure by virtue of prior invention.

II. The Invention

Figure 1:
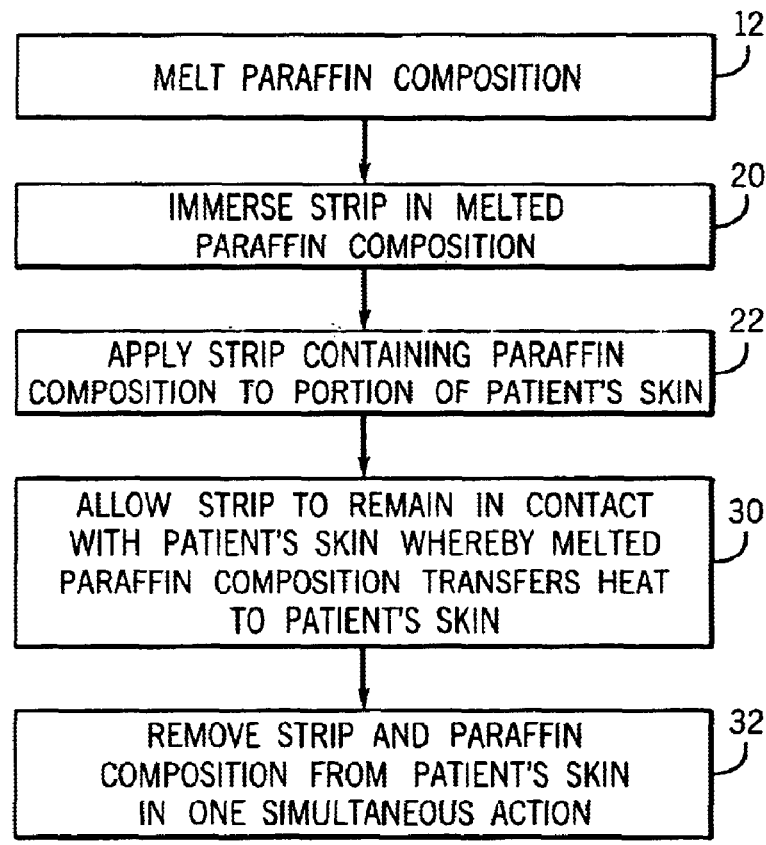
FIG. 1 depicts a flowchart that sets forth the steps of a hot paraffin treatment according to one embodiment of the present invention.

In general, the present invention encompasses articles and methods for providing therapeutic paraffin treatments to patients. In one embodiment, the invention is directed to methods of applying hot paraffin to the skin of a patient so that a therapeutic effect is achieved. FIG. 1 illustrates the steps of a method according to the invention set forth in flowchart form. In addition, FIGS. 2A–D depict in graphic form the corresponding steps described in the boxed text of FIG. 1.

Figure 2A:
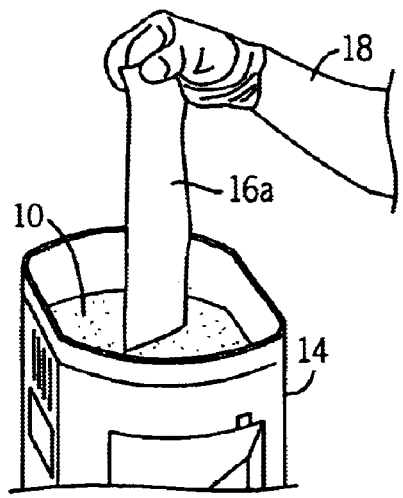
FIGS. 2 (A–D) illustrates the application of a paraffin strip to a patient's body part according to the present invention.
Figure 2B:
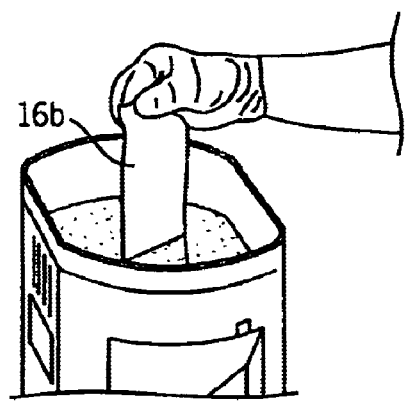

Referring now to FIGS. 1, 2A and 2B, a paraffin composition 10 is melted to a flowable state during an initial melting step 12. Paraffin compositions suitable for use in the present invention are well known in the art and are available from, for example: WR Medical Electronics, Co. under the federally registered mark THERAFFIN; HoMedics, Inc. under the federally registered mark HOMEDICS; Inverness, Corp. under the trade name INVERNESS; and Schering-Plough Healthcare Products, Inc. under the federally registered mark DR. SCHOLL'S. Paraffin compositions are heated to and maintained at a flowable state by any suitable heating means known in the art including a paraffin heating bath 14 as shown in FIGS. 2A–D. Melted paraffin compositions are generally heated and maintained at temperatures ranging from about 125° F. to about 130° F. A suitable paraffin heating bath for use with the invention is available from WR Medical Electronics Co., Stillwater, Minn. under the federally-registered trademark THERABATH. Another suitable bath is available under the federally registered trademark DR. SCHOLL'S (Thermal Therapy Paraffin Bath—Model DR5503).

Once the paraffin composition 10 has reached a flowable state, at least a portion of an absorptive strip 16a is immersed by a user 18 in paraffin composition 10 so that a volume of melted paraffin 10 is absorbed by strip 16a as shown in FIG. 2A and described in immersing step 20 of FIG. 1. Entire strip 16a may be immersed in melted paraffin composition 10 or substantially immersed with a portion of strip 16a gripped by the user not contacting melted paraffin 10.

Figure 2C:
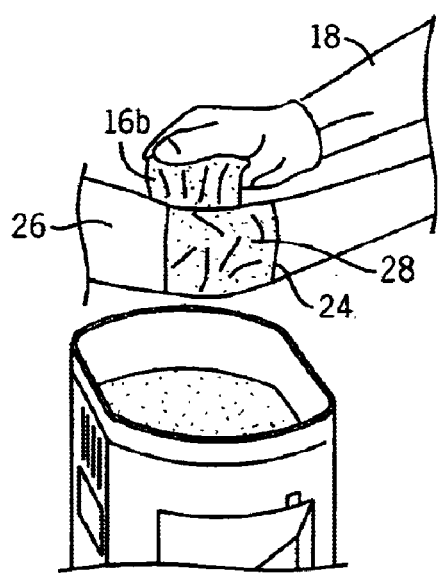
Figure 2D:
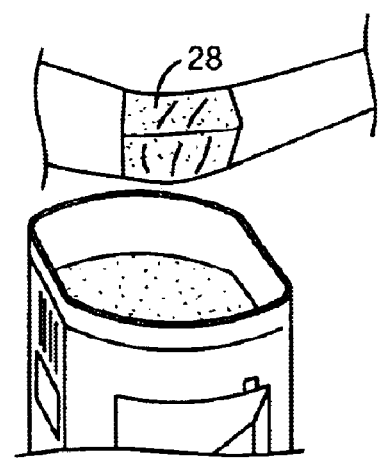

In FIG. 2B, user 18 lifts strip 16b from the pooled melted paraffin composition 10 to allow excess melted paraffin not absorbed by strip 16b to drip back into heating bath 14. As described in FIG. 1, user 18 then performs an application step 22 whereby strip 16b containing the melted paraffin composition 10 is contacted with a portion of skin 24 on a patient's exposed body part 26. FIG. 2C illustrates application step 22 in which user 18 wraps strip 16b around body part 26 to form a paraffin wrap 28. The completed wrap 28 is shown in FIG. 2D.

In the particular embodiment illustrated in FIGS. 2A–D, a single strip 16b is utilized in forming wrap 28. However, a plurality of strips may be employed in an alternative method according to the invention to form wrap 28. Furthermore, strip or strips 16b may not need to form a wrap that fully-encircles a body part 26 as illustrated in FIGS. 2A–D. In one embodiment, strip or strips 16b may contact a patient's skin so as to form a patch that covers but does not fully-encircle a body part. Such a patch is useful where the present invention is directed to a large body part such as the backbone, shoulder or hip where fully-encircling the body part is not practical and may not be possible due to restrictions in a patient's range of movement.

As described in box 30 of FIG. 1, strip 16b is subsequently allowed to remain in contact with a portion of the patient's skin 24 so that melted paraffin 10 transfers therapeutic heat content to the patient's skin 24 and underlying joints, muscles, etc. During this time period, the patient maintains body part 26 in a relatively stationary position without extensive movement of underlying joints and muscles.

While not required in all methods according to the invention, it is preferable that strip 16b is left in contact with skin 24 at least until paraffin composition 10 is reduced in heat content such that paraffin composition 10 approximates in temperature the temperature of skin 24 on which strip 16b is applied. At this point, heat transfer from strip 16b to the treated portion of skin is effectively at an end. Particular paraffin compositions may vary in the time necessary to reach this end point temperature, and additional factors such as heating bath temperature, external temperature, and volume of melted paraffin applied will determine the actual time needed which can be determined with minimal effort by one skilled in the art. A method for making such a determination is described in the Example provided below although one of skill in the art may make an approximation of the approximate time necessary by evaluating the perceived temperature, appearance and rigidity of strip 16b by the user's touch as well as by feedback from the patient him or herself. In one embodiment, strip 16b is allowed to contact skin 24 for a time period of at least five (5) minutes.

Data provided in the Example section below and depicted in FIG. 3 reveal that a paraffin-containing strip as described herein, and applied according to the present invention, acts as an insulator and maintains heat against the skin of a patient for a longer time period in comparison to traditional paraffin treatments (i.e., the body part dipping technique). A greater heat content is thus conveyed to underlying tissues by the present methods and materials and improved heat therapy is consequently achieved to, most importantly, the benefit of the patient.

Following a sufficient time period for effective heat transfer, a removal step 32 is then performed as described in FIG. 1 wherein strip 16b is removed from the portion of the patient's skin 24. In all embodiments of the present invention, removal step 32 entails the simultaneous removal of strip 16b including associated paraffin composition 10 together, in unitary fashion. This action is facilitated by the at least partially solidified paraffin composition 10 being contained within strip 16b. Removal may be by way of unwrapping or peeling strip 16b from the patient's skin or, alternatively, strip 16b may first be cut or slit using a cutting means to hasten quick removal of strip 16b with accompanying paraffin composition 10.

The stream-lined removal step of the present invention provides improved efficiencies including allowing the user to provide quicker and cleaner paraffin removal thereby speeding patient and work area clean-up. A user may be able to provide treatment to additional patients by lowering the total treatment time per individual patient allowing more patients per day to be treated. Alternatively, the period of time therapeutic heat is provided to each patient may be lengthened to provide improved therapeutic effects to each individual patient. Patient satisfaction is also improved due to a simplification of the paraffin removal process that, as described above, is traditionally a cumbersome and messy activity.

In one embodiment of the present invention, a method for providing therapeutic paraffin treatment includes melting a paraffin composition 10 to a flowable state and then immersing at least a portion of an absorptive strip 16a into the melted paraffin composition 10. Strip 16b containing the melted paraffin composition 10 is then applied to a portion of skin 24 on the patient wherein the portion of skin 24 overlies a body part 26 including at least a finger joint, a wrist, an elbow, a shoulder, a neck, a backbone, a hip, a knee, an ankle, or a toe joint. Strip 16b containing the melted paraffin composition 10 is allowed to remain in contact with the portion of skin 24 whereby the melted paraffin 10 transfers heat to the patient's skin 24. Strip 16b remains in contact with the portion of skin 24 for a sufficient amount of time for the paraffin composition 10 to solidify. Strip 16b is then removed from the portion of the patient's skin 24 wherein the paraffin composition 10 is contained by the strip 16b making removal of strip and paraffin composition simultaneous.

Methods according to the present invention are certainly envisioned to cover application to all portions of a patient's skin. In certain embodiments, it is preferable that the skin portion overlie a body part comprising, but not be limited to, a finger joint, a wrist, an elbow, a shoulder, a neck, a backbone, a hip, a knee, an ankle, or a toe joint. Medical afflictions of the joints, including arthritis, bursitis, fibrositis, tendonitis, chronic joint inflammation, are common in today's senior population and heat treatments have been found particularly helpful in alleviating or reducing pain associated with the majority of these maladies. In addition, paraffin heat treatments relax muscles, reduce muscle spasms, and stimulate blood circulation to affected areas thereby promoting physiological processes including healing.

While methods according to the invention have been described above, the present invention is additionally directed to the therapeutic paraffin strip 16b to be applied to a portion of a patient's skin to provide a therapeutic paraffin treatment. A therapeutic paraffin strip 16b according to the present invention includes: (a) an absorptive strip 16a; and (b) melted paraffin composition 10 contained within at least a portion of strip 16a. The therapeutic paraffin strip is applied to the portion of the patient's skin as shown and described previously so that the heat of the melted paraffin composition is transferred to the portion of the patient's skin to provide a therapeutic treatment according to the invention. As described above, the paraffin strip may take the form of a wrap 28 that is applied around a patient's body part 26. Wrap 28 may be comprised by a single strip 16b or a plurality of strips 16b, the exact nature of the wrap 28 is determined according to the judgment of the skilled user in view of the teachings provided herein.

In a preferred embodiment, the absorptive strip 16 is comprised of paper. The paper preferably exhibits an absorptive capacity for paraffin in the range of 1–25 grams paraffin/gram paper, more preferably 5–15 grams paraffin/gram paper, and most preferably 6–10 grams paraffin/gram paper. Suitable paper strips for use in the present invention are available from Graham Professional, a division of Little Rapids Corporation, Green Bay, Wis. under the trademark SPA ESSENTIALS. These particular strips are approximately 3.5" wide by 17" long. These particular strips provide an average paraffin absorptive capacity of 8.51 grams paraffin/gram paper (see Example 2).

In addition to possessing a degree of absorptive capacity for paraffin, strips useful in the present invention preferably display some degree of flexibility. For example, an above-described strip from Graham Professional exhibits a mean percentage stretch of between about 85–100%; these values represent a percentage change for the amount a strip may be stretched from an original dimension, in this case, the machine direction of the strip. Techniques for attaining such measurements, or those equivalent thereto, are well known by those skilled in the art. Stretchability, while not absolutely required for practice of the present invention, is a preferred quality in a strip according to the invention because stretchability allows strips to be snugly applied in a conforming manner without discomfort to the patient while strip/skin contact is kept at a maximum for optimal heat transfer.

Strips useful in the invention may be supplied for use as individual sheets or, alternatively, in a clip or roll form comprising a plurality of absorptive strips. The strips may be separable by perforations or supplied as a continuous sheet from which the user tears appropriate lengths. In a preferred embodiment, the particular strips described above from Graham Professional are provided in a clip that is approximately 3.5" wide, 4" long and 2" deep. The strips are folded into the clip in a continuous sheet with perforations at 17" lengths. Each clip contains approximately 40 strips.

Strips according to the invention are certainly not limited to paper construction but may comprise any suitable material having comparable absorptive or, more preferably, absorptive and stretch characteristics to those described above for paper embodiments. For example, non-woven materials suitable for constructing strips according to the present invention include spun-bond, melt-blown, spun-bond/melt-blown/spun-bond (SMS) composites and air-laid materials possessing absorptive characteristics comparable to the paper embodiments described above. Other suitable materials include, but are not limited to, materials such as foam or cotton, in particular, cotton woven into strips, or, alternatively, in the form of gauze, bands, or pads which may serve as equivalents to the strip in various embodiments.

Finally, the present invention encompasses a therapeutic regimen provided in a systematic manner to a patient that includes at least a therapeutic paraffin treatment according to the present invention. A therapeutic regimen includes all currently available therapeutic techniques available at a spa, homeopathic therapy provider, out-patient therapy provider, or equivalent thereof. A regimen includes a systematic series of treatments each aimed at improving the health and mind of a patient. Such series of treatments are commonly offered as packages to be provided, for example, over a single day or over a planned time course of several days, weeks, or months. Examples of treatments that may be offered in a therapeutic regimen along with hot paraffin treatment according to the invention include, but are not limited to, massage therapy, exercise therapy, hot rock therapy, vichy shower, steam canopy, dry brush exfoliation, mud or clay masks and wraps, herbal wraps, and enzymatic or chemical peels.

The following Examples are offered by way of illustration and not by way of limitation.

III. EXAMPLES

Example 1

This example demonstrates the improved heat transfer observed with a paraffin treatment according to the invention as compared to a traditional paraffin "dip" treatment. Two applications of melted paraffin wax to skin were as follows:

1. A temperature probe was attached to a person's hand such that it came into contact with the person's skin. The person then dipped the person's hand into the melted wax three times, each time dipping it sufficiently that the probe was covered by wax. Then the wax was allowed to solidify in air. Temperature readings were recorded at 15 second intervals for five minutes.
2. A temperature probe was attached to a person's skin such that it came into the contact with the person's skin. Paper strips 3.5" wide (paper strips available from Graham Professional, as described above) were then dipped into the melted wax and applied to the person's hand so that the probe was covered. Three of the dipped paper strips were used. Temperature readings were recorded at 15 second intervals for five minutes.

Figure 3:
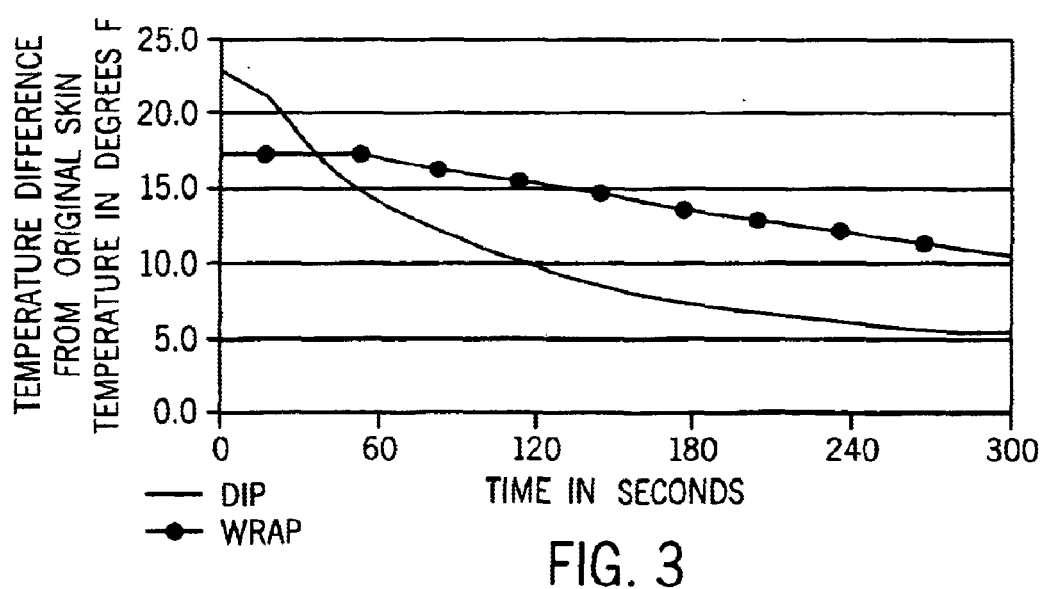
FIG. 3 shows a graph of temperature difference from original skin (° F.) versus time (seconds) for a hand treated with a traditional paraffin dip technique and a hand treated by paraffin wrapping according to the invention.

In FIG. 3, a graph is shown illustrating the results obtained for the above-described procedures. Temperature difference from original skin (° F.) is plotted against time (seconds) for the hand treated with the traditional paraffin dip technique. Data is likewise plotted for a hand treated by a paraffin treatment according to the present invention. The results indicate that the traditional dip technique exhibited a greater initial temperature spike, but then dropped more quickly over time relative to the new method according to the invention described herein. In contrast, the paraffin treatment according to the invention had a lower initial temperature spike, but held the temperature at an elevated level for a longer time period as compared to the traditional technique. Upon consideration of the data plotted in FIG. 3, it can be concluded that the technique according to the invention provides a higher temperature at the patient's skin for a longer period of time as compared to the traditional paraffin dip technique. This example clearly illustrates the insulative properties of strips and wraps fashioned and applied according to the invention.

Example 2

This example provides a test to determine paraffin absorbency capacity for a strip according to the invention. The test was performed by completely immersing a strip (e.g., a 3.5"×17" strip available from Graham Professional, as described above) of known mass into a bath containing fully melted paraffin maintained at 125° F. to about 130° F. The particular bath used was available under the federally registered trademark DR. SCHOLL'S (Thermal Therapy Paraffin Bath—Model DR5503). The strip was then taken out of the bath and allowed to drip above the surface of the bath for a time period often (10) seconds. The strip was immediately re-weighed and the difference between the original pre-immersion weight and the final weight was divided by the weight of the pre-immersion strip to obtain results in grams paraffin per grams strip material. The paraffin absorbency capacity for 3.5"×17" paper strips available from Graham Professional (cat. no. 50113) described above as being preferred for use in the invention, exhibited an average paraffin absorbency of 8.51 grams paraffin/grams paper. The test was performed in triplicate to obtain a range of 8.06–8.87 grams paraffin/grams paper with a standard deviation of 0.219.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for providing a therapeutic paraffin treatment to a patient, comprising the steps of:

(a) melting a paraffin composition to a flowable state;

(b) immersing at least a portion of an absorptive strip into the melted, flowable paraffin composition, thereby permitting the strip to absorb some of the flowable paraffin composition; and (c) applying said strip containing the flowable paraffin composition to a portion of skin of the patient, whereby the still melted paraffin transfers heat to the patient's skin.

2. A method according to claim 1 further comprising, after the step of applying the strip to the portion of the skin of the patient, allowing the strip containing the melted paraffin composition to remain in contact with said portion of skin and thereafter removing the strip from the portion of the patient's skin wherein the paraffin composition is contained by the strip.

3. A method according to claim 1, wherein the removal of the strip and paraffin from the patient's skin is substantially simultaneous.

4. A method according to claim 3 wherein the strip containing the melted paraffin composition remains in contact with said portion of skin for at least five (5) minutes.

5. A method according to claim 3 wherein the portion of skin on which said strip containing the melted paraffin composition is applied overlies a body part including at least a finger joint, a wrist, an elbow, a shoulder, a neck, a backbone, a hip, a knee, an ankle, or a toe joint.

6. A method according to claim 2 wherein the absorptive strip is comprised by paper.

7. A method according to claim 6 wherein said paper has a paraffin absorptive capacity in the range of about six (6) to ten (10) grams paraffin per gram material of paper.

8. A method according to claim 1 wherein said absorptive strip has a paraffin absorptive capacity in the range of about six (6) to ten (10) grams paraffin per gram material of strip.

9. A method according to claim 2 wherein the strip containing the melted paraffin composition remains in contact with said portion of skin for a sufficient amount of time for said paraffin composition to solidify before removal.

10. A method according to claim 1 wherein the portion of patient's skin continuously extends around a body part and the application of said strip containing the melted paraffin composition includes wrapping the strip around said body part to form said strip into a wrap surrounding said body part.

11. A method according to claim 10 wherein a plurality of absorptive strips are applied to the portion of the patient's skin.

12. A therapeutic paraffin strip to be applied to a portion of a patient's skin to provide a therapeutic paraffin treatment to the patient, comprising:

(a) an absorptive paper strip exhibiting a mean percentage of stretch between about 85–100%; and (b) a melted paraffin composition contained within at least a portion of said strip;

whereby the therapeutic paraffin strip is applied to the portion of the patient's skin such that the heat of the melted paraffin composition is transferred to said portion of the patien's skin to provide a therapeutic treatment.

13. A therapeutic paraffin strip according to claim 12 wherein the absorptive strip has a paraffin absorptive capacity in the range of about six (6) to ten (10) grams paraffin per gram material of strip.

14. A method for providing a therapeutic paraffin treatment to a patient, comprising the steps of:

(a) melting a paraffin composition to a flowable state;

(b) immersing at least a portion of a stretchable, absorptive strip into the melted paraffin composition;

(c) applying said strip containing the still melted paraffin composition to a portion of skin on the patient wherein the portion of skin overlies a body part including at least a finger joint a wrist, an elbow, a shoulder, a neck, backbone, a hip, a knee, an ankle, or a toe joint;

(d) allowing the strip containing the melted paraffin composition to remain in contact with said portion of skin whereby the melted paraffin transfers heat to the patient's skin; and (e) removing the strip from the portion of the patient's skin wherein the paraffin composition is contained by the strip making removal of strip and paraffin composition simultaneous.

\* \* \* \* \*